US012329580B2

(12) United States Patent
Roundhill et al.

(10) Patent No.: US 12,329,580 B2
(45) Date of Patent: Jun. 17, 2025

(54) CONTEXTUAL MULTIPLANAR RECONSTRUCTION OF THREE-DIMENSIONAL ULTRASOUND IMAGING DATA AND ASSOCIATED DEVICES, SYSTEMS, AND METHODS

(71) Applicant: KONINKLIJKE PHILIPS N.V., Eindhoven (NL)

(72) Inventors: David Nigel Roundhill, Woodinville, WA (US); Tobias Klinder, Uelzen (DE); Alexander Schmidt-Richberg, Hamburg (DE); Matthias Lenga, Mainz (DE); Eliza Teodora Orasanu, Hamburg (DE); Cristian Lorenz, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 166 days.

(21) Appl. No.: 17/908,289

(22) PCT Filed: Feb. 22, 2021

(86) PCT No.: PCT/EP2021/054251
§ 371 (c)(1),
(2) Date: Aug. 31, 2022

(87) PCT Pub. No.: WO2021/175629
PCT Pub. Date: Sep. 10, 2021

(65) Prior Publication Data
US 2023/0054610 A1 Feb. 23, 2023

Related U.S. Application Data

(60) Provisional application No. 62/985,534, filed on Mar. 5, 2020.

(51) Int. Cl.
*A61B 8/00* (2006.01)
(52) U.S. Cl.
CPC .............. *A61B 8/483* (2013.01); *A61B 8/523* (2013.01)
(58) Field of Classification Search
CPC ......... A61B 8/483; A61B 8/523; A61B 8/145; G01S 15/8993; G01S 7/52073; G06T 19/003

See application file for complete search history.

(56) References Cited

U.S. PATENT DOCUMENTS

| 4,173,007 A | 10/1979 | McKeighen et al. |
| 6,280,387 B1 * | 8/2001 | Deforge ................. A61B 8/13 128/916 |

(Continued)

FOREIGN PATENT DOCUMENTS

| JP | H07155328 A | 6/1995 |
| WO | 2007049207 A1 | 5/2007 |
| WO | 2011117788 A1 | 9/2011 |

OTHER PUBLICATIONS

International Search Report and Written Opinion for PCT/EP2021/054251; Mailing date: May 26, 2021, 9 pages.

(Continued)

*Primary Examiner* — Oommen Jacob

(57) ABSTRACT

An ultrasound imaging system includes a processor circuit in communication with an ultrasound transducer configured to receive three-dimensional ultrasound data of an anatomy, and generate a target image corresponding to a target image plane of the anatomy, and a plurality of adjacent images corresponding to image planes adjacent to the target image plane along a simulated motion path. The processor circuit is further configured to display the target image, receive a user input representative of a direction of motion along the simulated motion path, and display an adjacent image of the (Continued)

plurality of adjacent images corresponding to the direction of motion. Accordingly, the user can observe the target image in its spatial context by scanning through the target image and one or more adjacent images on the display as if the ultrasound transducer were being scanned along the simulated motion path.

16 Claims, 8 Drawing Sheets

(56) References Cited

U.S. PATENT DOCUMENTS

| | | | |
|---|---|---|---|
| 6,443,896 B1 | 9/2002 | Detmer | |
| 7,061,484 B2* | 6/2006 | Bailey | G06T 3/067 |
| | | | 345/419 |
| 7,771,354 B2 | 8/2010 | Thiele | |
| 9,107,607 B2* | 8/2015 | Hansegard | G06T 15/08 |
| 10,905,396 B2* | 2/2021 | Cox | A61B 8/5246 |
| 2003/0055328 A1* | 3/2003 | Paladini | G06T 11/001 |
| | | | 600/407 |
| 2003/0105401 A1* | 6/2003 | Jago | A61B 8/467 |
| | | | 600/443 |
| 2006/0114254 A1 | 6/2006 | Day et al. | |
| 2007/0255139 A1* | 11/2007 | Deschinger | A61B 8/465 |
| | | | 600/443 |
| 2009/0238404 A1 | 9/2009 | Orderud et al. | |
| 2009/0304250 A1* | 12/2009 | McDermott | A61B 8/463 |
| | | | 382/131 |
| 2010/0026808 A1 | 2/2010 | Kagehiro et al. | |
| 2010/0121189 A1* | 5/2010 | Ma | A61B 8/463 |
| | | | 600/437 |
| 2011/0172536 A1* | 7/2011 | Do | A61B 8/14 |
| | | | 600/443 |
| 2012/0176365 A1* | 7/2012 | Hansegard | A61B 8/523 |
| | | | 345/419 |
| 2013/0226544 A1* | 8/2013 | Mcconaghy | G06F 30/20 |
| | | | 703/2 |
| 2013/0249913 A1 | 9/2013 | Smout et al. | |
| 2014/0015573 A1 | 1/2014 | Ross et al. | |
| 2014/0198979 A1* | 7/2014 | Hamarneh | G06T 7/174 |
| | | | 382/154 |
| 2015/0042657 A1 | 2/2015 | Smith-Casem et al. | |
| 2015/0209599 A1* | 7/2015 | Schlosser | A61B 8/54 |
| | | | 600/427 |
| 2015/0262353 A1 | 9/2015 | Yoo et al. | |
| 2016/0070436 A1* | 3/2016 | Thomas | G06T 7/0012 |
| | | | 715/771 |
| 2019/0027266 A1 | 1/2019 | Shah et al. | |
| 2023/0054610 A1* | 2/2023 | Roundhill | G01S 15/8993 |

OTHER PUBLICATIONS

Shekhar, R. et al., "Cine MPR: interactive multiplanar reformatting of four-dimensional cardiac data using hardware-accelerated texture mapping", EEE Transactions on Information Technology in Biomedicine, 2003, vol. 7, No. 4, pp. 384-393.
Redmon, J. et al., You Only Look Once: Unified, Real-Time Object Detection, arXiv:1506.02640, 2016, 10 pages.
Schmidt-Richberg, A. et al., "Offset regression networks for view plane estimation in 3D fetal ultrasound", Proceedings of the SPIE, 2019, Abstract Only.

* cited by examiner

CONTEXTUAL MULTIPLANAR RECONSTRUCTION OF THREE-DIMENSIONAL ULTRASOUND IMAGING DATA AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2021/054251, filed on Feb. 22, 2021, which claims the benefit of U.S. Provisional Patent Application No. 62/985,536, filed on Mar. 5, 2020. These applications are hereby incorporated by reference herein.

TECHNICAL FIELD

The present disclosure relates generally to the acquisition and processing of ultrasound images and, in particular, to systems and methods for reconstructing two-dimensional images from three-dimensional ultrasound image data.

BACKGROUND

Ultrasound imaging is frequently used to obtain images of internal anatomical structures of a patient. Ultrasound systems typically comprise an ultrasound transducer probe that includes a transducer array coupled to a probe housing. The transducer array is activated to vibrate at ultrasonic frequencies to transmit ultrasonic energy into the patient's anatomy, and then receive ultrasonic echoes reflected or backscattered by the patient's anatomy to create an image. Such transducer arrays may include various layers, including some with piezoelectric materials, which vibrate in response to an applied voltage to produce the desired pressure waves. These transducers may be used to successively transmit and receive several ultrasonic pressure waves through the various tissues of the body. The various ultrasonic responses may be further processed by an ultrasonic imaging system to display the various structures and tissues of the body.

Physicians and sonographers often desire to obtain certain views of the patient's body such that the imaging plane of the ultrasound transducer is aligned to obtain image of a particular combination and orientation of anatomical structures. For example, in fetal ultrasound biometry, a sonographer obtains a variety of images or views of the fetal anatomy to perform measurements and assessments of the fetus' development. Examples of these views include transventricular, trans-cerebellar, and trans-thalamic image planes. Conventionally, these target views are achieved manually by an experienced sonographer positioning and orienting the ultrasound transducer while watching a real-time or near real-time image stream of the field of view of the ultrasound transducer.

When the sonographer determines that a desired view is shown, the sonographer may freeze or save the image frame to memory, and/or continue to move the probe around the target view to ensure that the desired view is actually achieved. The temporal and spatial information gained in conventional two-dimensional ultrasound imaging procedures can be useful in assessing an image, as it provides important context information in addition to a dedicated two-dimensional image to be used in the biometry assessment, for example. Thus, the sonographer has a spatial awareness of the location of the plane they are searching for based on their knowledge of the images of anatomy that are near or adjacent to the plane they want to capture. Intrinsically, the confidence that the target plane is correctly detected is based on the temporal context in the two-dimensional image stream. Nonetheless, this traditional two-dimensional acquisition workflow strongly depends on the individual skills of the sonographer.

Alternatively, some ultrasound imaging systems allow for a target view to be obtained automatically from a three-dimensional ultrasound data set. Automated image reconstruction techniques can be beneficial because they depend less on the individual skills of the sonographer. For example, an ultrasound transducer array may be used to sweep out a three-dimensional volume and obtain a three-dimensional ultrasound data set representative of the volume while the sonographer holds the ultrasound probe body at a fixed position and orientation. A multiplanar reconstruction (MPR) technique can be used to generate a two-dimensional image associated with a desired view. While MPR imaging techniques beneficially allow for less-experienced sonographers to achieve a target view, one drawback of MPR is that an image may not be correctly reconstructed by the system, and the user does not have the spatial/temporal context to confirm whether or not the reconstructed image is correct or optimal. By contrast, conventional two-dimensional ultrasound imaging provides the sonographer with real-time feedback and spatial context as the user can make manual adjustments to the probe to evaluate the imaged volume around the target view.

SUMMARY

Aspects of the present disclosure provide ultrasound systems and devices that provide for multiplanar reconstructions of images with contextual visualizations to increase confidence in plane selection during an ultrasound imaging procedure. For example, in one embodiment, an ultrasound imaging system includes a processor circuit in communication with an ultrasound transducer configured to obtain a three-dimensional ultrasound data set. The processor circuit is configured to reconstruct, from the ultrasound data set, a target image or image slice corresponding to a target view or image plane, such as an apical view of the heart, trans-cerebellar, trans-thalamic, etc. Additionally, the processor circuit is configured to reconstruct, from the same three-dimensional ultrasound data set, one or more adjacent images corresponding to planes that are adjacent to the target image plane. The adjacent images are reconstructed such that the adjacent image and the target image correspond to image planes that are on a simulated motion path that also corresponds to the target image. For example, the simulated motion path may be representative of a linear translation, a sweeping or fanning motion, a tilt, rocking motion, and/or a rotation of the ultrasound probe, with the target image plane extending from a point along the simulated motion path. The reconstructed adjacent images can be output to a display such that a user can view the adjacent images part of a sequence with the target image to obtain spatial, contextual information about the target image. In that regard, in some embodiments, the user can scan through the target image and one or more adjacent images on the display as if the ultrasound transducer were being scanned along the simulated motion path. Thus, the user may determine that the target image reconstructed from the image data is correctly-aligned with the target image plane, or determine that adjustments could be made to reconstruct the target image to be correctly aligned with the target image plane.

According to one embodiment of the present disclosure, an ultrasound imaging apparatus includes a processor circuit configured to: receive, from an ultrasound probe communicatively coupled to the processor circuit, three-dimensional ultrasound data of an anatomy; generate, from the three-dimensional ultrasound data, a target image corresponding to a target image plane of the anatomy; generate, from the three-dimensional ultrasound data, a plurality of adjacent images corresponding to image planes adjacent to the target image plane along a simulated motion path, wherein the target image and the plurality of adjacent images comprise two-dimensional images based on the three-dimensional ultrasound data; output, to a display in communication with the processor circuit, the target image; receive a user input representative of a direction of motion along the simulated motion path; and output, to the display, an adjacent image of the plurality of adjacent images corresponding to the direction of motion.

In some embodiments, the apparatus further includes the ultrasound probe. In some embodiments, the processor circuit is configured to: interpolate between a position and orientation of the target image and a position and orientation of the adjacent image to generate an interpolated image; and output the interpolated image to the display. In some embodiments, the processor circuit is configured to: determine a direction of uncertainty relative to the target image plane; and determine the simulated motion path based on the determined direction of uncertainty. In some embodiments, the processor circuit is configured to apply a covariance matrix to the three-dimensional ultrasound data to determine the direction of uncertainty.

In some embodiments, the processor circuit is configured to: identify, from the three-dimensional ultrasound data, an image plane of interest different from the target image and the adjacent image; and determine the simulated motion path based on the target image, the adjacent image, and the image of interest. In some embodiments, the processor circuit is configured to output the image of interest in response to receiving the user input. In some embodiments, the plurality of adjacent images comprises a plurality of parallel adjacent images associated with a plurality of parallel adjacent image planes. In some embodiments, the processor circuit is configured to generate the target image to exclude an anatomical feature. In some embodiments, the processor circuit is configured to generate the adjacent image to include the anatomical feature. In some embodiments, the processor circuit is further configured to output, to the display, a graphical representation of an adjacent image plane associated with the adjacent image, wherein the graphical representation includes: a diagrammatic view of a body portion associated with the target image; and an indicator of the adjacent image plane overlaid on the diagrammatic view of the body portion.

According to another embodiment, a method for reconstructing ultrasound images includes: receiving, three-dimensional ultrasound data of an anatomy obtained by an ultrasound probe; generating, from the three-dimensional ultrasound data, a target image corresponding to a target image plane of the anatomy; generating, from the three-dimensional ultrasound data, a plurality of adjacent images corresponding to image planes adjacent to the target image plane along a simulated motion path, wherein the target image and the plurality of adjacent images comprise two-dimensional images based on the three-dimensional ultrasound data; outputting, to a display, the target image; receiving a user input representative of a direction of motion along the simulated motion path; and outputting, to a display, an adjacent image of the plurality of adjacent images corresponding to the direction of motion.

In some embodiments, generating the plurality of adjacent images comprises interpolating between a position and orientation of the target image and a position and orientation of the adjacent image to generate an interpolated image. In some embodiments, the method further comprises outputting the interpolated image to the display. In some embodiments, generating the plurality of adjacent images comprises: determining a direction of uncertainty relative to the target image plane; and determining the simulated motion path based on the determined direction of uncertainty. In some embodiments, determining the direction of uncertainty comprises applying a covariance matrix to the three-dimensional ultrasound data.

In some embodiments, the method further comprises identifying, from the three-dimensional ultrasound data, an image of interest different from the target image and the adjacent image; and determining the simulated motion path based on the target image, the adjacent image, and the image of interest. In some embodiments, the method further comprises outputting the image of interest in response to receiving the user input. In some embodiments, generating the plurality of adjacent images comprises generating a plurality of parallel adjacent images associated with a plurality of parallel adjacent image planes. In some embodiments, generating the target image comprises generating the target image to exclude an anatomical feature. In some embodiments, generating the adjacent image comprises generating the adjacent image to include the anatomical feature. In some embodiments, the method further comprises outputting, to the display, a graphical representation of an adjacent image plane associated with the adjacent image. In some embodiments, the graphical representation includes: a diagrammatic view of a body portion associated with the target image; and an indicator of the adjacent image plane overlaid on the diagrammatic view of the body portion.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
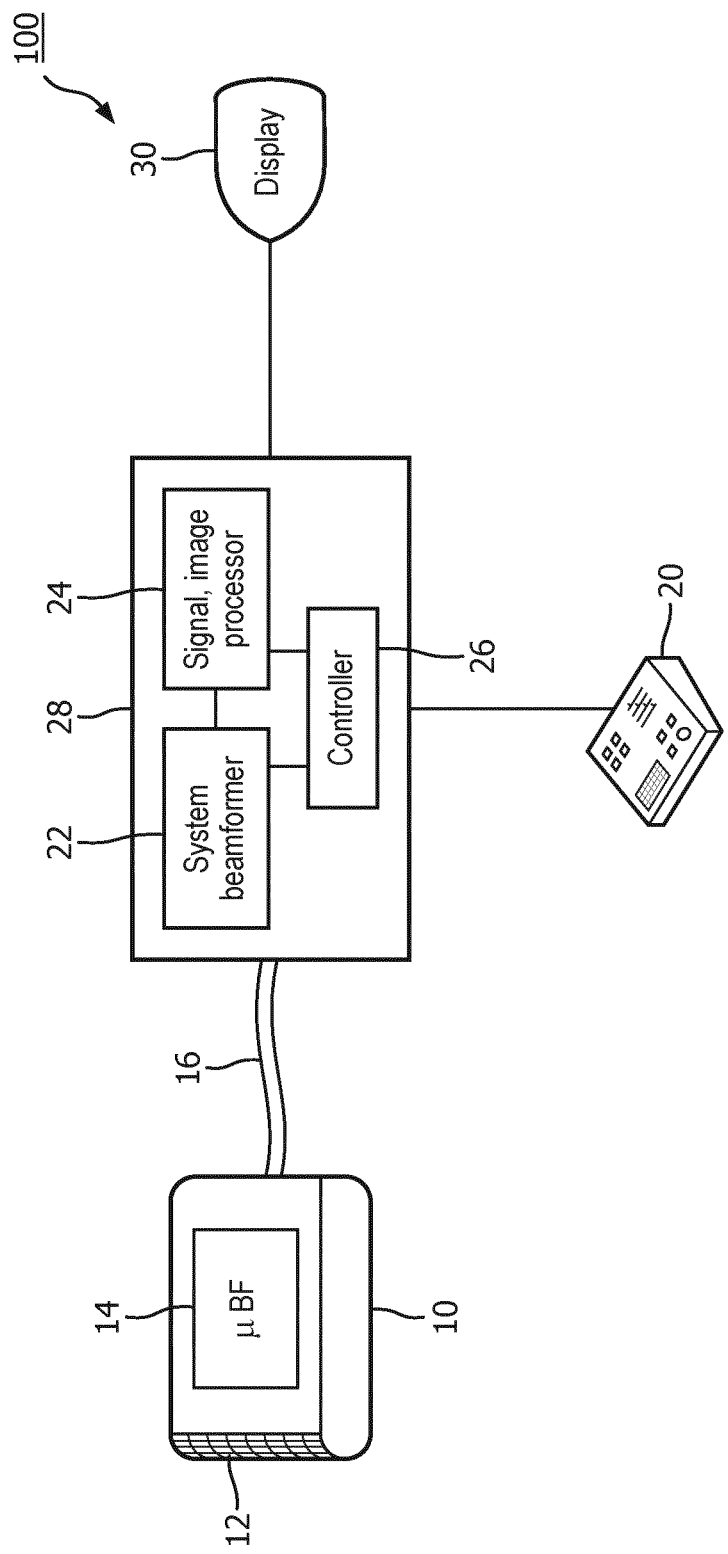
FIG. 1 is a schematic diagram of an ultrasound imaging system, according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

In FIG. 1, an ultrasound system 100 according to embodiments of the present disclosure is shown in block diagram form. An ultrasound imaging apparatus or ultrasound probe 10 has a transducer array 12 comprising a plurality of ultrasound transducer elements or acoustic elements. In some instances, the array 12 may include any number of acoustic elements. For example, the array 12 can include between 1 acoustic element and 100000 acoustic elements, including values such as 2 acoustic elements, 4 acoustic elements, 36 acoustic elements, 64 acoustic elements, 128 acoustic elements, 300 acoustic elements, 812 acoustic elements, 3000 acoustic elements, 9000 acoustic elements, 30,000 acoustic elements, 65,000 acoustic elements, and/or other values both larger and smaller. In some instances, the acoustic elements of the array 12 may be arranged in any suitable configuration, such as a linear array, a planar array, a curved array, a curvilinear array, a circumferential array, an annular array, a phased array, a matrix array, a one-dimensional (1D) array, a 1.X dimensional array (e.g., a 1.5D array), or a two-dimensional (2D) array. The array of acoustic elements (e.g., one or more rows, one or more columns, and/or one or more orientations) can be uniformly or independently controlled and activated. The array 12 can be configured to obtain one-dimensional, two-dimensional, and/or three-dimensional images of patient anatomy.

Although the present disclosure refers to synthetic aperture external ultrasound imaging using an external ultrasound probe, it will be understood that one or more aspects of the present disclosure can be implemented in any suitable ultrasound imaging probe or system, including external ultrasound probes and intraluminal ultrasound probes. For example, aspects of the present disclosure can be implemented in ultrasound imaging systems using a mechanically-scanned external ultrasound imaging probe, an intracardiac (ICE) echocardiography catheter and/or a transesophageal echocardiography (TEE) probe, a rotational intravascular ultrasound (IVUS) imaging catheter, a phased-array IVUS imaging catheter, a transthoracic echocardiography (TTE) imaging device, or any other suitable type of ultrasound imaging device.

Figure 2:
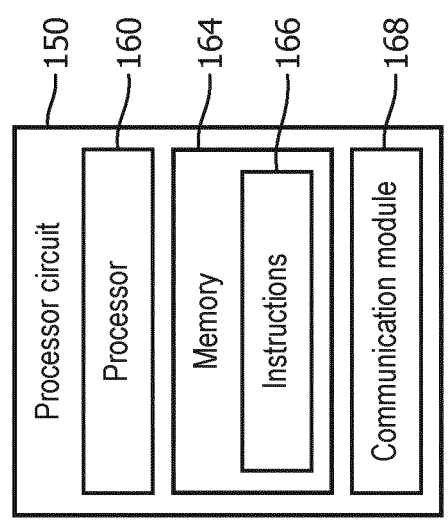
FIG. 2 is a schematic diagram of a processor circuit, according to embodiments of the present disclosure.

Referring again to FIG. 1, the acoustic elements of the array 12 may comprise one or more piezoelectric/piezoresistive elements, lead zirconate titanate (PZT), piezoelectric micromachined ultrasound transducer (PMUT) elements, capacitive micromachined ultrasound transducer (CMUT) elements, and/or any other suitable type of acoustic elements. The one or more acoustic elements of the array 12 are in communication with (e.g., electrically coupled to) electronic circuitry 14. In some embodiments, such as the embodiment of FIG. 1, the electronic circuitry 14 can comprise a microbeamformer (μBF). In other embodiments, the electronic circuitry comprises a multiplexer circuit (MUX). The electronic circuitry 14 is located in the probe 10 and communicatively coupled to the transducer array 12. In some embodiments, one or more components of the electronic circuitry 14 can be positioned in the probe 10. In some embodiments, one or more components of the electronic circuitry 14, can be positioned in a computing device or processing system 28. The computing device 28 may be or include a processor, such as one or more processors in communication with a memory. As described further below, the computing device 28 may include a processor circuit as illustrated in FIG. 2. In some aspects, some components of the electronic circuitry 14 are positioned in the probe 10 and other components of the electronic circuitry 14 are positioned in the computing device 28. The electronic circuitry 14 may comprise one or more electrical switches, transistors, programmable logic devices, or other electronic components configured to combine and/or continuously switch between a plurality of inputs to transmit signals from each of the plurality of inputs across one or more common communication channels. The electronic circuitry 14 may be coupled to elements of the array 12 by a plurality of communication channels. The electronic circuitry 14 is coupled to a cable 16, which transmits signals including ultrasound imaging data to the computing device 28.

In the computing device 28, the signals are digitized and coupled to channels of a system beamformer 22, which appropriately delays each signal. The delayed signals are then combined to form a coherent steered and focused receive beam. System beamformers may comprise electronic hardware components, hardware controlled by software, or a microprocessor executing beamforming algorithms. In that regard, the beamformer 22 may be referenced as electronic circuitry. In some embodiments, the beamformer 22 can be a system beamformer, such as the system beamformer 22 of FIG. 1, or it may be a beamformer implemented by circuitry within the ultrasound probe 10. In some embodiments, the system beamformer 22 works in conjunction with a microbeamformer (e.g., electronic circuitry 14) disposed within the probe 10. The beamformer 22 can be an analog beamformer in some embodiments, or a digital beamformer in some embodiments. In the case of a digital beamformer, the system includes A/D converters which convert analog signals from the array 12 into sampled digital echo data. The beamformer 22 generally will include one or more microprocessors, shift registers, and or digital or analog memories to process the echo data into coherent echo signal data. Delays are effected by various means such as by the time of sampling of received signals, the write/read interval of data temporarily stored in memory, or by the length or clock rate of a shift register as described in U.S. Pat. No. 4,173,007 to McKeighen et al., the entirety of which is hereby incorporated by reference herein. Additionally, in some embodiments, the beamformer can apply appropriate weight to each of the signals generated by the array 12. The beamformed signals from the image field are processed by a signal and image processor 24 to produce 2D or 3D images for display on an image display 30. The signal and image processor 24 may comprise electronic hardware components, hardware controlled by software, or a microprocessor executing image processing algorithms. It generally will also include specialized hardware or software which processes received echo data into image data for images of a desired display format such as a scan converter. In some embodiments, beamforming functions can be divided between different beamforming components. For example, in some embodiments, the system 100 can include a microbeamformer located within the probe 10 and in communication with the system beamformer 22. The microbeamformer may perform preliminary beamforming and/or signal processing that can reduce the number of communication channels required to transmit the receive signals to the computing device 28.

Control of ultrasound system parameters such as scanning mode (e.g., B-mode, M-mode), probe selection, beam steering and focusing, and signal and image processing is done under control of a system controller 26 which is coupled to various modules of the system 100. The system controller 26 may be formed by application specific integrated circuits (ASICs) or microprocessor circuitry and software data storage devices such as RAMs, ROMs, or disk drives. In the case of the probe 10, some of this control information may be provided to the electronic circuitry 14 from the computing device 28 over the cable 16, conditioning the electronic circuitry 14 for operation of the array as required for the particular scanning procedure. The user inputs these operating parameters by means of a user interface device 20.

In some embodiments, the image processor 24 is configured to generate images of different modes to be further analyzed or output to the display 30. For example, in some embodiments, the image processor can be configured to compile a B-mode image, such as a live B-mode image, of an anatomy of the patient. In other embodiments, the image processor 24 is configured to generate or compile an M-mode image. An M-mode image can be described as an image showing temporal changes in the imaged anatomy along a single scan line.

It will be understood that the computing device 28 may comprise hardware circuitry, such as a computer processor, application-specific integrated circuit (ASIC), field-programmable gate array (FPGA), capacitors, resistors, and/or other electronic devices, software, or a combination of hardware and software. In some embodiments, the computing device 28 is a single computing device. In other embodiments, the computing device 28 comprises separate computer devices in communication with one another.

FIG. 2 is a schematic diagram of a processor circuit 150, according to embodiments of the present disclosure. The processor circuit 150 may be implemented in the computing device 28, the signal and image processor 24, the controller 26, and/or the probe 10 of FIG. 1. As shown, the processor circuit 150 may include a processor 160, a memory 164, and a communication module 168. These elements may be in direct or indirect communication with each other, for example via one or more buses.

The processor 160 may include a central processing unit (CPU), a digital signal processor (DSP), an ASIC, a controller, an FPGA, another hardware device, a firmware device, or any combination thereof configured to perform the operations described herein. The processor 160 may also be implemented as a combination of computing devices, e.g., a combination of a DSP and a microprocessor, a plurality of microprocessors, one or more microprocessors in conjunction with a DSP core, or any other such configuration.

The memory 164 may include a cache memory (e.g., a cache memory of the processor 160), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 164 includes a non-transitory computer-readable medium. The memory 164 may store instructions 166. The instructions 166 may include instructions that, when executed by the processor 160, cause the processor 160 to perform the operations described herein with reference to the processor 28 and/or the probe 10 (FIG. 1). Instructions 166 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 168 can include any electronic circuitry and/or logic circuitry to facilitate direct or indirect communication of data between the processor 28, the probe 10, and/or the display 30. In that regard, the communication module 168 can be an input/output (I/O) device. In some instances, the communication module 168 facilitates direct or indirect communication between various elements of the processor circuit 150 and/or the processing system 106 (FIG. 1A).

Figure 3:
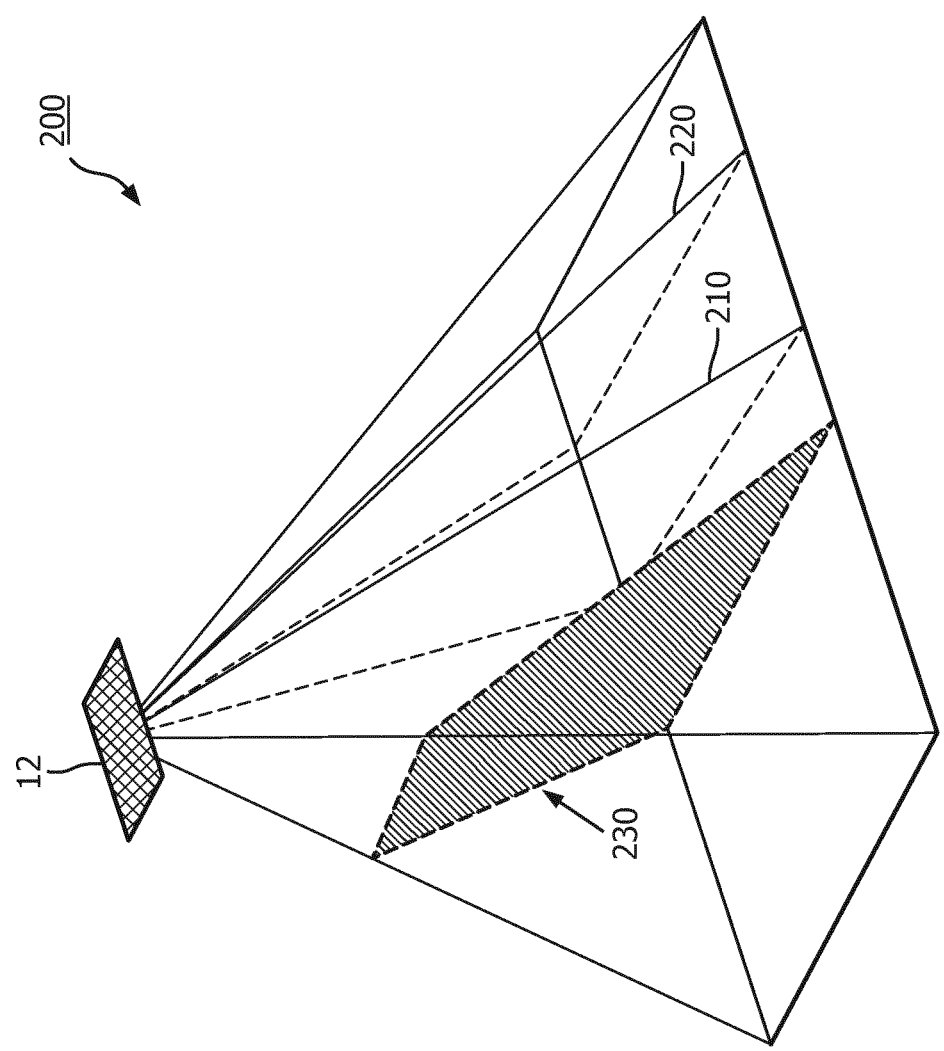
FIG. 3 is a diagrammatic view of image slices reconstructed from a three-dimensional ultrasound data set of a volume, according to aspects of the present disclosure.

As mentioned above, some ultrasound imaging systems are configured to obtain three-dimensional ultrasound data of a volume of the patient. In some embodiments, an ultrasound imaging system comprises an ultrasound transducer comprising an array of one or more transducer elements, where the ultrasound transducer is configured to scan or sweep through a volume of the patient to obtain a three-dimensional ultrasound data set of the volume. This three-dimensional ultrasound data can be used to generate three-dimensional images or models of the anatomy. Alternatively, two-dimensional images corresponding to a variety of imaging planes that intersect the volume can be reconstructed from the three-dimensional ultrasound data. In that regard, FIG. 3 shows a plurality of image slices 210, 220 forming a three-dimensional ultrasound data set of a volume 200. The slices 210, 220 are obtained as part of an image sequence using an ultrasound transducer array 12. In the illustrated embodiment, the array 12 comprises a two-dimensional array of ultrasound transducer elements that can be controlled as a phased array to electronically steer ultrasonic beams of acoustic energy to sweep out the image slices 210, 220, in a plurality of corresponding image planes. In other embodiments, the ultrasound transducer array 12 may comprise a single ultrasound transducer element, or a one-dimensional array of transducer elements in which the transducer 12 manually scans in one or more degrees of freedom to acquire the three-dimensional data set of the volume 200.

In FIG. 3, the image slices 210, 220 may correspond to image planes of an image sequence performed by the ultrasound transducer. Thus, the three-dimensional data set of the volume 200 may be formed by acquiring ultrasound data in a step-wise fashion where an image slice is obtained by steering or sweeping the ultrasound beams or scan lines across the corresponding image plane, and combining the plurality of different image slices 210, 220 to form the three-dimensional data set. In some embodiments, the slices 210, 220 may be combined into a three-dimensional image by determining interpolated intensity values from the different slices 210, 220, such that an intensity value can be determined for any location (e.g., in a Cartesian coordinate system) in the three-dimensional image. Additionally, FIG. 3 shows a reconstructed image 230, which is reconstructed from the three-dimensional data set after the image sequence has completed scanning the volume 200. Thus, the reconstructed image 230, in contrast to the image slices 210, 220, does not directly correspond to the two-dimensional segments of the three-dimensional imaging sequence, and does not represent an image plane that intersects the ultrasound transducer 12. For example, the reconstructed image 230 may represent an image plane passing through the volume if the ultrasound transducer 12 had been moved to a different position and orientation relative to the volume 200. However, in some embodiments, an image can be reconstructed from the three-dimensional data set that is representative of an imaging plane that does intersect the ultrasound transducer 12.

In some embodiments, multiplanar reconstruction (MPR) can be used to reconstruct, from the three-dimensional ultrasound data, a target image corresponding to a target view or imaging plane of the patient (e.g., trans-ventricular, trans-cerebellar, trans-thalamic, apical view, etc.). For example, MPR may be used to generate the reconstructed image 230 shown in FIG. 3. MPR can be performed using input from various image processing techniques, including artificial intelligence (A.I.), machine learning, and/or deep learning techniques, to identify a two-dimensional cross section in the three-dimensional ultrasound data that includes a combination and/or arrangement of anatomical structures associated with a particular view. In that regard, while MPR involves generating an image for an identified plane within a three-dimensional data set, the estimation or identification of the plane that will be used in the MPR image may be referred to as plane estimation (PE). Methods for PE are described in, for example, U.S. Pat. No. 6,443, 896, issued Sep. 3, 2002, U.S. Publication No. 2014/ 0155737, filed Aug. 13, 2012, U.S. Publication No. 2010/ 0268085, filed Nov. 13, 2008, and U.S. Publication No. 2019/0272667, filed Jun. 12, 2017, and Joseph Redmon, et al., "You Only Look Once: Unified, Real-Time Object Detection," The IEEE Conference on Computer Vision and Pattern Recognition (CVPR), 2016, pp. 779-788, each of which is hereby incorporated by reference in its entirety.

While PE beneficially allows for the automatic reconstruction of a target image with less input from the sonographer (i.e., manual adjustment of probe to achieve the target view), PE techniques may have some drawbacks. For example, the sonographer may not be able to easily confirm that an image generated using PE and displayed as an MPR is the correct or optimal view. In that regard, because the target image is automatically reconstructed and displayed with little or no interaction from the sonographer, the sonographer may lack spatial context that would otherwise be gained if the sonographer was manually scanning the probe across the anatomy around the target view. Thus, confidence that the correct image has been acquired may be diminished. Further, an incorrect or suboptimal image plane may be selected by the PE algorithm, and the sonographer may not be able to easily identify what adjustments are to be made to more completely achieve a desired view.

Accordingly, the present disclosure provides devices, systems, and associated methods for providing contextual visualizations associated with automatically reconstructed two-dimensional images, such as images generated from PE. In particular, the present disclosure provides for automated image reconstruction techniques that allow for a target image to be generated and displayed, while still providing spatial contextual information to the sonographer so that the sonographer can confirm that the correct image plane has been chosen to automatically reconstruct the target image. For example, in an exemplary workflow, the sonographer places an ultrasound probe configured to obtain three-dimensional ultrasound data on the skin of the patient at a location generally associated with the target image plane. A three-dimensional data set of a volume of the patient is acquired, and the sonographer can set the probe down. A processing system and/or processor circuit analyzes the three-dimensional ultrasound data using, for example, PE and/or MPR, to identify, reconstruct, or otherwise generate a target image associated with a target image plane or view, such as the trans-cerebellar view. The target image can then be displayed using MPR to the user, which may allow the user to make measurements or assessments of the anatomy in the target image.

Further, the processor circuit is configured to provide spatial context for the target image by generating a plurality of adjacent images that are associated with imaging planes adjacent to the target image plane. The adjacent images are generated such that the target image and the adjacent images all correspond to a common simulated motion path or trajectory. The simulated motion path is computed so that scanning through the adjacent images and the target image simulates physical scanning or pacing of the ultrasound probe around the target image plane. As described below, in an exemplary embodiment, the sonographer may scan through the adjacent images along the simulated motion path using a keyboard, track ball, or other interface device as though the user was manually moving the probe around the target image plane. Accordingly, the sonographer may have increased confidence that the processor circuit has correctly and/or optimally reconstructed the target image. Further, by scanning through the reconstructed adjacent image, the sonographer may be able to determine whether the target image reconstruction should be revised or redone.

Accordingly, embodiments of the present disclosure provide for an experience of seeing two-dimensional images that are proximate or near to a target plane. The two-dimensional images can be created or reconstructed from a three-dimensional data set, thereby recreating a traditional experience in order to improve the sonographer's confidence that the desired anatomically planes were correctly detected by the automated procedure. Specifically, the systems and methods described herein enable the simulation of an ultrasound probe movement which allows a smooth transition from one automatically detected plane to another automatically detected plane. These smooth image transitions emulate the transducer movements, which are familiar to the sonographer from a standard two-dimensional ultrasound exam. Smooth transitions between different view planes can be achieved, for example, by interpolating the plane parameters (normal and offset vectors) and thus obtaining continuous spline trajectories for two-dimensional plane displacement in three-dimensional space.

The sequence of image frames shown to the user may be a compilation of adjacent MPRs determined based on geometric spacing. In some embodiments, the sequence of images or image frames shown includes a selection of geometrically adjacent images that have been selected, e.g., by an A.I. algorithm, to be somewhat similar to the target image plane. For example, in case of a fetal head biometry assessment, where multiple images are captured at different image planes, the proposed dynamic representation can be used to perform interpolation between respective image plane parameters. These interpolated images can be used to dynamically transition from one selected plane to the other, thus performing a transition through the three-dimensional volume in which the planes are located.

Once the target image is generated the three-dimensional data set, one or more adjacent images could be generated in a number of ways. In one embodiment, adjacent image frames correspond to parallel planes to the target plane. In applications where more than one plane of interest is within the volume (e.g., abdominal and thoracic, trans-ventricular (TV), trans-cerebellar (TC), trans-thalamic (TT)), a set of adjacent image frames can be created by interpolating between the planes of interest. For this purpose, interpolation can be done in a fixed order, e.g., always going from TT to TV, or by finding the two closest planes. In some embodiments, an A.I.—based approach for plane detection provides a way of measuring uncertainty such that a direction of highest uncertainty may be identified. Images may be interpolated along the direction of highest uncertainty. This would leverage an efficient manual correction of automatically determined images.

In applications where the anatomical target image plane is required to exclude certain anatomical structures or features, the adjacent images can be generated such that at least one adjacent image includes of the anatomical feature to be excluded, the other adjacent images are generated to show the anatomical feature disappearing from the field of view (e.g. the cerebellum in the TV plane of the fetal brain). For educational or reporting purpose, the adjacent image set can be displayed with a schematic anatomical view, since the three-dimensional volume together with the estimated plane geometries and located anatomical objects provides sufficient information for the registration to a three-dimensional anatomical model.

Figure 4:
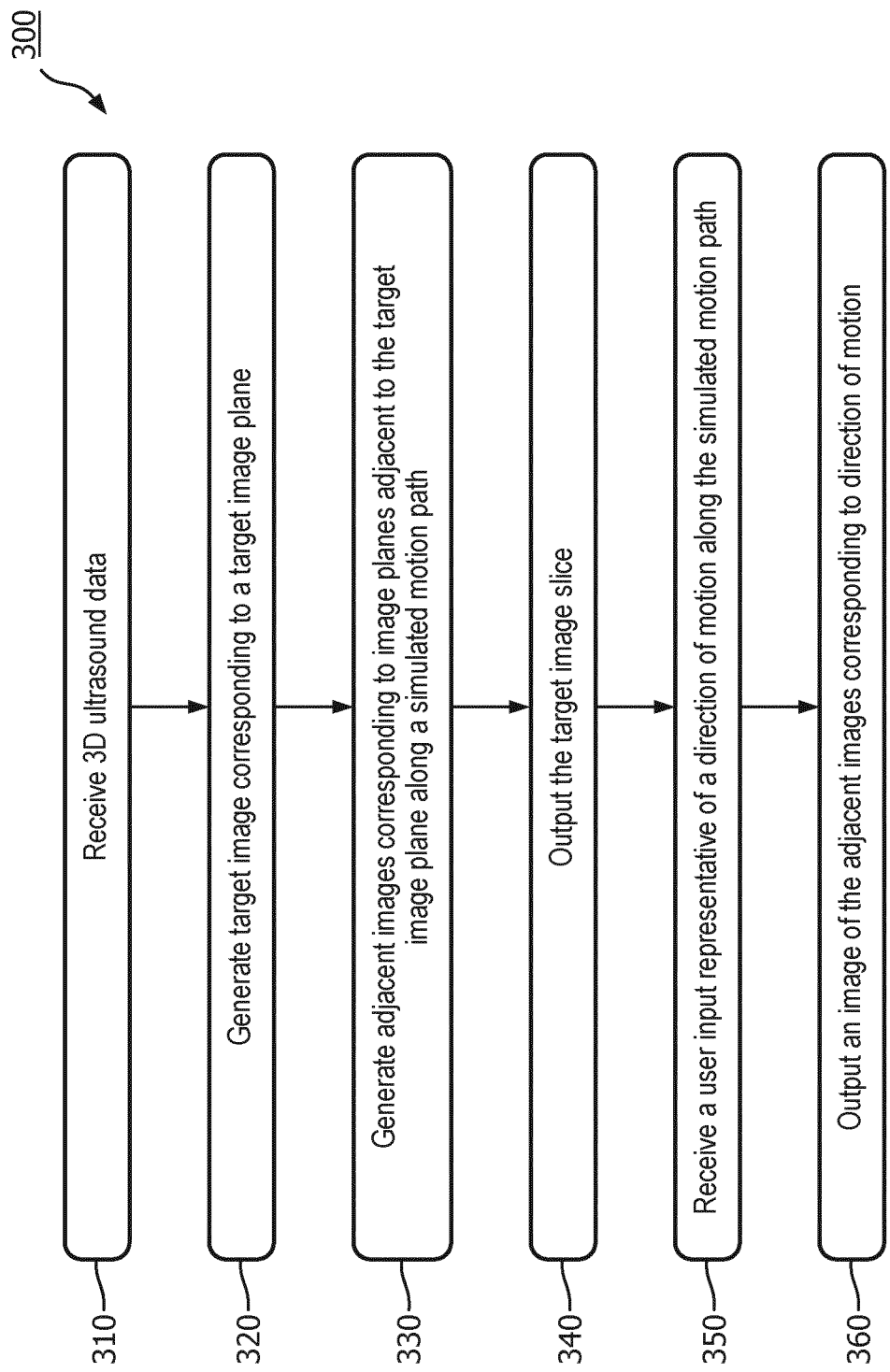
FIG. 4 is a flow diagram illustrating a method for generating and displaying contextual multiplanar image reconstructions from a three-dimensional ultrasound dataset, according to aspects of the present disclosure.

FIG. 4 is a flow chart illustrating a method 300 for providing spatial context for automated ultrasound image plane reconstructions. It will be understood that one or more steps of the method 300 may be performed by the ultrasound imaging system 100 shown in FIG. 1, and/or the processor circuit 150 shown in FIG. 2, for example. In step 310, a processor circuit receives, from an ultrasound probe communicatively coupled to the processor circuit, three-dimensional ultrasound data of an anatomy of a patient. In some embodiments, the ultrasound data may be obtained during a fetal ultrasound procedure, a trans-thoracic ultrasound feature, a cardiac ultrasound procedure, or any other suitable procedure. The ultrasound probe includes an ultrasound transducer having an array of one or more ultrasound transducer elements. In some embodiments, the ultrasound transducer comprises a one-dimensional array, a 1.5-dimensional array, a 1.X dimensional array, a two-dimensional array, or any other suitable type of array of ultrasound transducer elements. In some embodiments, the array is mechanically scanned to obtain a plurality of image slices of the volume. In some embodiments, the array is operated as a solid-state array, or a phased array configured to electronically scan across the volume. In some embodiments, the three-dimensional ultrasound data is made up of a plurality of two-dimensional images or image slices. In some embodiments, the three-dimensional ultrasound data is made up of a plurality of individual scan lines of ultrasound data.

In some embodiments, the ultrasound data received by the processor circuit comprises raw ultrasound signals or data. In other embodiments, the ultrasound data received by the processor circuit comprises beamformed, partially beamformed, and/or filtered ultrasound data. In some embodiments, the processor circuit receives the ultrasound data directly from the ultrasound probe. In some embodiments, the ultrasound data is first received by a memory, which stores the ultrasound data, and the processor circuit then receives the ultrasound data from the memory. Accordingly, in some embodiments, the processor circuit receives the ultrasound data indirectly from the ultrasound probe after being stored in the memory.

In some embodiments, step 310 includes generating a user instruction to be output to a user output device or interface (e.g., display, speaker, etc.) to first place the ultrasound probe in a general location such that a target view is within a three-dimensional field of view of the ultrasound probe. For example, the user instruction may include a diagrammatic illustration of the patient's body, and an indicator showing how to position and orient the probe relative to the patient's body.

In step 320, the processor circuit generates, from the three-dimensional ultrasound data, a target image corresponding to a target image plane of the anatomy. For example, as described above, the target image plane or view to be achieved is the trans-ventricular, trans-cerebellar, or trans-thalamic view of a fetus, an apical view of a patient's heart, or any other suitable view. In some embodiments, generating the target image comprises using a PE and/or MPR process to automatically reconstruct the target image. However, a variety of image processing and recognition techniques can be used, including A.I. techniques, machine learning techniques, deep learning techniques, state machines, etc. In some embodiments, generating the target image may include comparing the three-dimensional image data to a model of the anatomy. In some embodiments, generating the target image includes comparing various portions of the three-dimensional ultrasound data representative of different cross sections of the three-dimensional field of view to one or more exemplary images of the anatomy.

In step 330, the processor circuit generates, from the three-dimensional ultrasound data, one or more adjacent images corresponding to image planes adjacent to the target image plane along a simulated motion path, wherein the target image and the one or more adjacent images comprise two-dimensional images based on the three-dimensional ultrasound data. The adjacent image(s) generated during step 330 can be used to provide contextual information to the user, which can accompany the display of the target image generated in step 320.

As mentioned above, the simulated motion path may be representative of a physical adjustment or movement of the ultrasound probe, such as a translation, linear movement, compression, rotation, fanning, sweeping, rocking, or any other suitable type of motion. In some embodiments, step 330 includes determining or computing the simulated motion path. For example, the processor circuit may determine or compute the simulated motion path based on the target view to be reconstructed. The simulated motion path may be a parameter for reconstructing the adjacent images, in that the simulated motion path or trajectory defines the spatial relationships between the adjacent images to be reconstructed from the three-dimensional ultrasound data of the volume. In some embodiments the path will be defined by a set of points which are smoothly connected to a curved line, e.g. based on spline interpolation techniques. The points set may be a set of anatomical landmarks, such as organs to be inspected, or may follow an anatomical structure such as the spine. In another embodiment, the path may be constructed such that it shows, for education, the degrees of freedom when maneuvering the transducer, such as translating the transducer position on the skin surface, or rotating/tilting the transducer around its three principle axes.

Figure 5:
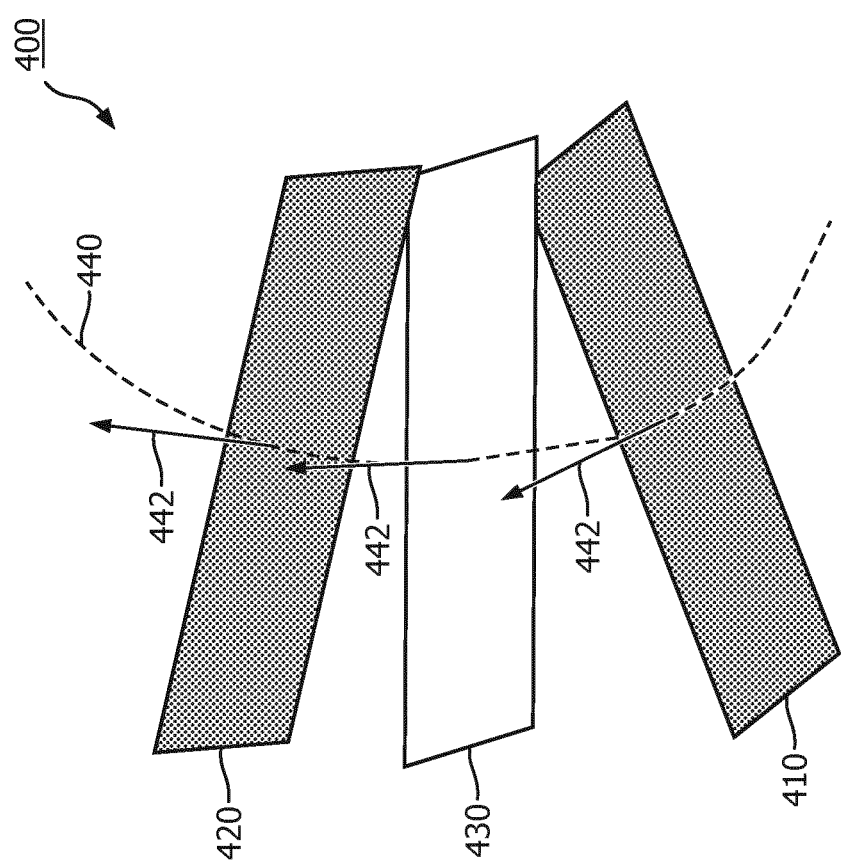
FIG. 5 is a diagrammatic view of a plurality of image planes or image slices corresponding to a simulated motion path, according to aspects of the present disclosure.

FIG. 5 shows a target image 410, an adjacent image 420, and an interpolated image 430 that correspond to a simulated motion path 440. In the illustrated embodiment, the darker rectangles are representative of image planes 410, 420 reconstructed from the ultrasound data. The white rectangle is representative of an interpolated image plane 430 generated using the target image 410 and the adjacent image 420. The target image 410, adjacent image 420 and the interpolated image 430 are generated to correspond to a simulated motion path 440. In that regard, the simulated motion path 440 may be determined or computed by the processor circuit, and may be representative of a simulated type of movement of the ultrasound probe (i.e., as if the ultrasound probe were to be physically scanned across a volume). In the illustrated embodiment, the simulated motion path 440 is representative of a mixed tilting/rocking movement of the ultrasound probe. The orthogonal axes 442 of the images 410, 420, 430, are tangential to the simulated motion path 440 at the point at which the images 410, 420, 430 intersect the simulated motion path 440.

Figure 6C:
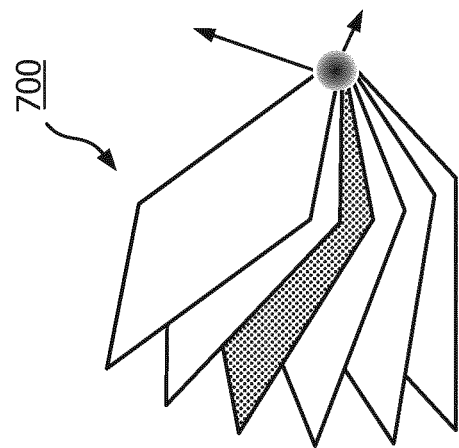
FIG. 6C is a diagrammatic view of a plurality of image planes or image slices corresponding to a simulated curved motion path, according to aspects of the present disclosure.
Figure 6B:
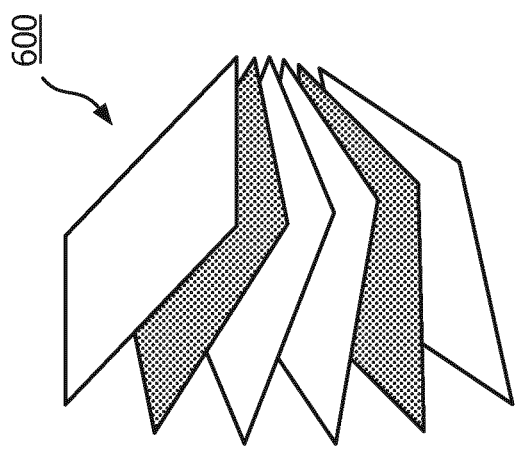
FIG. 6B is a diagrammatic view of a plurality of image planes or image slices corresponding to a simulated curved motion path, according to aspects of the present disclosure.
Figure 6A:
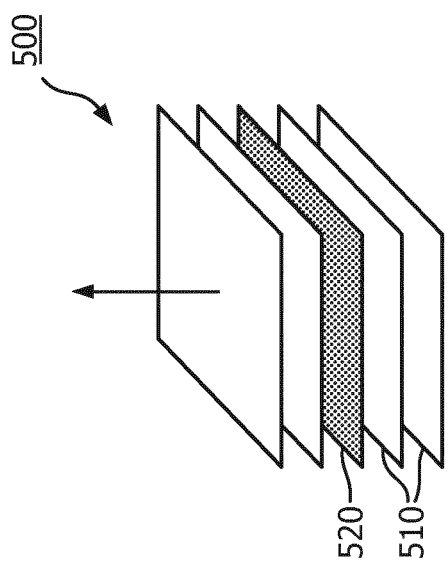
FIG. 6A is a diagrammatic view of a plurality of image planes or image slices corresponding to a simulated linear motion path, according to aspects of the present disclosure.

It will be understood that a variety of simulated motion paths are contemplated by the present disclosure. The simulated motions paths may be pre-determined or selected based on the target imaging plane desired to be obtained. In that regard, FIGS. 6A, 6B, and 6C are representative of image planes, both reconstructed and interpolated, that correspond to three different simulated motion paths. For example, in FIG. 6A, the image slices include a reconstructed image slice 510 represented by a dark rectangle, and interpolated images 520, represented by the white rectangles. The image slices 510, 520 are associated with a simulated linear motion path. Accordingly, the images correspond to image planes that are parallel to each other and spaced from each other. In FIG. 6B, the images 600 are associated with a simulated curved motion path, which includes a combination of simulated tilting and translation of the ultrasound probe. In FIG. 6C, the images 700 are associated with a simulated curved motion path, which includes a simulated tilting of the ultrasound probe. In some embodiments, the simulated motion path is determined or computed to include more than a single type of motion along its length. For example, a simulated motion path may be computed such that multiple image planes of interest (e.g., TC, TV, TT) would be obtained by the simulated movement of the probe along the motion path. Thus, the simulated motion path may be computed to have different segments associated with different types of simulated movements (e.g., translation, rocking, tilting, rotation, compression, etc.). In some embodiments, the processor circuit is configured to identify, from the three-dimensional ultrasound data, an image of interest different from the target image, and determine the simulated motion path based on the target image plane, the adjacent image plane, and the image plane of interest. The processor circuit can then output the image of interest to the display in response to receiving a user input, as further described below.

As shown in FIGS. 5 and 6A-6C, the processor circuit may be configured to generate one or more interpolated images (e.g., 430, FIG. 5) to accompany the one or more adjacent images (410, 420, FIG. 5). In that regard, in some instances, three-dimensional image data of a volume may be relatively sparse. For example, with conventional two-dimensional imaging procedures, the ultrasound probe may be capable of obtaining and displaying approximately 30 frames per second. Accordingly, sonographers may be accustomed to the ability to view two-dimensional views with a high degree of temporal and spatial resolution. However, because ultrasound imaging procedures are constrained by the speed of sound, the number of scan lines that can be obtained in a given amount of time is limited. Thus, for three-dimensional ultrasound imaging, temporal and/or spatial resolution may be reduced compared to two-dimensional ultrasound imaging. Therefore, ultrasound data points (e.g., voxels) available for the reconstruction of adjacent images may be limited.

Figures 7, 8:
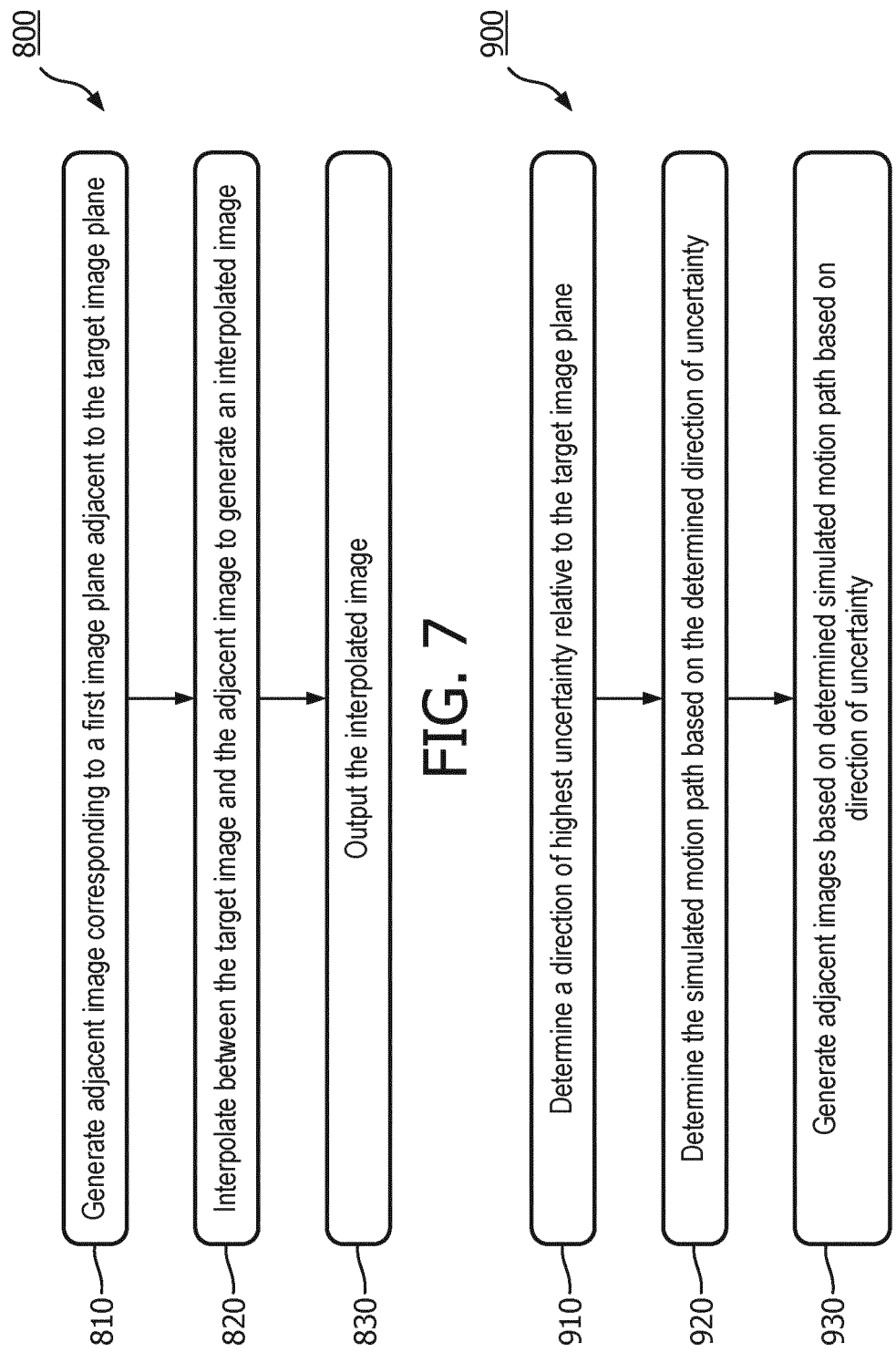
FIG. 7 is a flow diagram illustrating a method for generating interpolated image slices for a contextual multiplanar image reconstruction sequence, according to aspects of the present disclosure.
FIG. 8 is a flow diagram illustrating a method for reconstructing image slices based on a direction of uncertainty for a contextual multiplanar image reconstruction sequence, according to aspects of the present disclosure.

The present application provides that one or more images may be interpolated using one or more reconstructed image frames. In that regard, FIG. 7 provides a flow chart illustrating a method 800 for generating and outputting an interpolated image. It will be understood that one or more steps of the method 800 may be performed by the ultrasound imaging system 100 shown in FIG. 1, and/or the processor circuit 150 shown in FIG. 2, for example. In step 810, the processor circuit generates an adjacent image frame or image slice corresponding to a first image plane adjacent to the target image plane. Referring to FIG. 5, the target image and the adjacent image are reconstructed from the three-dimensional ultrasound data, as described above. In that regard, the adjacent image frame may be generated from a three-dimensional image that was created by interpolating the intensity values from a set of two-dimensional image slices obtained of a volume by an ultrasound imaging system. In some embodiments, the interpolation of the two-dimensional images is made with respect to a Cartesian coordinate system or grid. The target image and the adjacent image may be generated or reconstructed using MPR.

Referring to FIGS. 5 and 8, in step 820, the processor circuit interpolates the image position and orientation between the position and orientation of target image 410 and the adjacent image 420 to then generate the image 440 as an MPR at the interpolated position and orientation. In some aspects, the MPR image 440 is generated based on the interpolated intensity values of the three-dimensional image, as described above. As shown in FIG. 5, the adjacent images and the interpolated image are all generated to correspond to the simulated motion path 440. Accordingly, the orthogonal axis 442 of the interpolated image, like the reconstructed adjacent images, is tangential to the curved simulated motion path. In other words, the target image plane, the adjacent image plane, and the interpolated image plane are all orthogonal to the simulated motion path at the points at which the planes intersect the simulated motion path. In step 830, the processor circuit outputs the interpolated image to the display. For example, the processor circuit may be configured to generate one or more interpolated images between a target image and an adjacent image, and/or between adjacent images, and arrange the adjacent and interpolated images to form an image stack that can be scrolled or scanned through in response to the input from a user. For example, in some embodiments, as the sonographer scrolls up or down using a mouse, track ball, etc., the processor circuit incrementally updates the display based on the extent of the input. For example, the speed at which the sonographer rotates the track ball or swipes across a track pad may determine the speed at which the processor circuit updates the display with successive adjacent and interpolated images. Thus, the sonographer may have a similar amount of control to scanning through adjacent image planes as the sonographer would have had using a traditional two-dimensional imaging approach (i.e., without MPR). This type of visualization may provide for a familiar imaging experience while leveraging the workflow advantages of automated image reconstruction.

For example, referring again to FIG. 6A, the interpolated image frames 510 can supplement the reconstructed adjacent image frames 520 to provide a smoother, or more natural scanning visualization of the image planes adjacent to a target image plane. Thus, in some embodiments, the processor circuit is configured to interpolate between a target image and an adjacent image, or between two adjacent images, to generate the interpolated image. The interpolated image can then be output to the display in response to a user input indicating a direction of motion along the simulated motion path. In an exemplary embodiment, the interpolated image is generated by the processor circuit. The interpolated image is representative of an intermediate image plane in the volume between two reconstructed images generated directly from the three-dimensional ultrasound data. The interpolated image is associated with the same simulated motion path as the reconstructed adjacent image(s). Accordingly, as the user scans through the adjacent and interleaved interpolated images, the result is an image stream that more closely resembles manually scanning across a target region of an imaged volume, as performed in two-dimensional imaging procedures.

The interpolated images may be obtained by interpolation of the plane normal vectors and the plane offset vectors. The interpolation may be performed based on the position and orientation associated with each of the reconstructed images to obtain an interpolated plane position and normal. The intensity values of the 3D grid corresponding to the reconstructed images can then be interpolated to generate the intensity values for the interpolated plane. In some embodiments, motion vectors may be computed for individual pixels to generate the interpolated image. Methods and techniques for generating interpolated image frames can be found at least in U.S. Pat. No. 7,771,354, issued Aug. 10, 2010, the entirety of which is hereby incorporated by reference.

In step 340, the processor circuit outputs the target image slice to a display in communication with the processor circuit. As described below, the processor circuit may output a graphical user interface to the display, wherein the GUI includes the target image. In step 350, the processor circuit receives a user input representative of a direction of motion along the simulated motion path. For example, the processor circuit may receive the user input via a user input device in communication with the processor circuit. The user input device may include a mouse, keyboard, trackball, microphone, touch-screen display, track pad, physical button, or any other suitable type of user input device. In that regard, the user input may be provided by the sonographer by pressing an arrow key on a keyboard, where the arrow direction corresponds to a direction along the simulated motion path (e.g., forward, backward). In some embodiments, the user input is received by a scrolling device, such as a mouse, track ball, or track pad. The direction of the scrolling may correspond to the direction along the simulated motion path. However, it will be understood that any suitable user input could be used to indicate the direction of motion along the simulated path.

In step 360, the processor circuit outputs an adjacent image from the plurality of adjacent images that corresponds to the direction of motion. For example, in some embodiments, the target image is first output to the display. The sonographer then uses the user input device to scan forward or backward along the simulated direction of motion, and the processor circuit outputs one or more adjacent images generated in step 330. Accordingly, the sonographer can control the display of the reconstructed images to scan forward and backward along the simulated motion path as if the user was manually scanning the ultrasound probe along the motion path, but after the ultrasound image data has already been obtained and the ultrasound probe has been set down. Using this process, the sonographer is given the benefit of both (1) automated reconstruction of a target image from a three-dimensional data set, and (2) ability to gain spatial context to confirm that the automatically reconstructed target image is correctly and/or optimally reconstructed.

In determining or computing the simulated motion path, it may be beneficial to identify a simulated path that is relevant to providing confidence assessment that the automatically reconstructed target image is correctly determined. In that regard, the simulated motion path may be determined based on a determination of a direction of uncertainty relative to the target image plane. FIG. 8 is a flow diagram of a method 900 for determining a simulated motion path based on a determination of a direction of uncertainty. It will be understood that one or more steps of the method 900 may be performed by the ultrasound imaging system 100 shown in FIG. 1, and/or the processor circuit 150 shown in FIG. 2, for example. In step 910, the processor circuit determines a direction of uncertainty relative to the target image plane. In some embodiments, the processor circuit determines the direction of uncertainty relative to the target image plane by applying a covariance matrix to the three-dimensional ultrasound data. In step 920, the simulated motion path is generated by the processor circuit based on the determined direction of uncertainty. In some embodiments, the processor circuit may determine a plurality of directions of uncertainty. In some embodiments, the processor circuit may determine a direction or vector of highest uncertainty. In other embodiments, the processor circuit determines a direction of median uncertainty, average uncertainty, minimum uncertainty, and/or any other suitable relative measure of uncertainty selected from one or more determined directions or vectors of uncertainty. In step 930, the processor circuit generates one or more adjacent images based on the simulated motion path determined in step 920, which is based on the determined direction of uncertainty. With the adjacent images (and/or interpolated images) generated based on the determined direction of uncertainty, the sonographer may be more likely to identify incorrectly-aligned target images, or to determine probe movements and adjustments to generate the target image such that it is aligned with a target view or target image plane. Further details on determining a direction associated with uncertainty in MPR procedures can be found in Alexander Schmidt-Richberg, et al., "Offset regression networks for view plane estimation in 3D fetal ultrasound," Proc. SPIE, Vol. 10949, id. 109493K (Mar. 15, 2019), the entirety of which is incorporated by reference.

Figure 9:
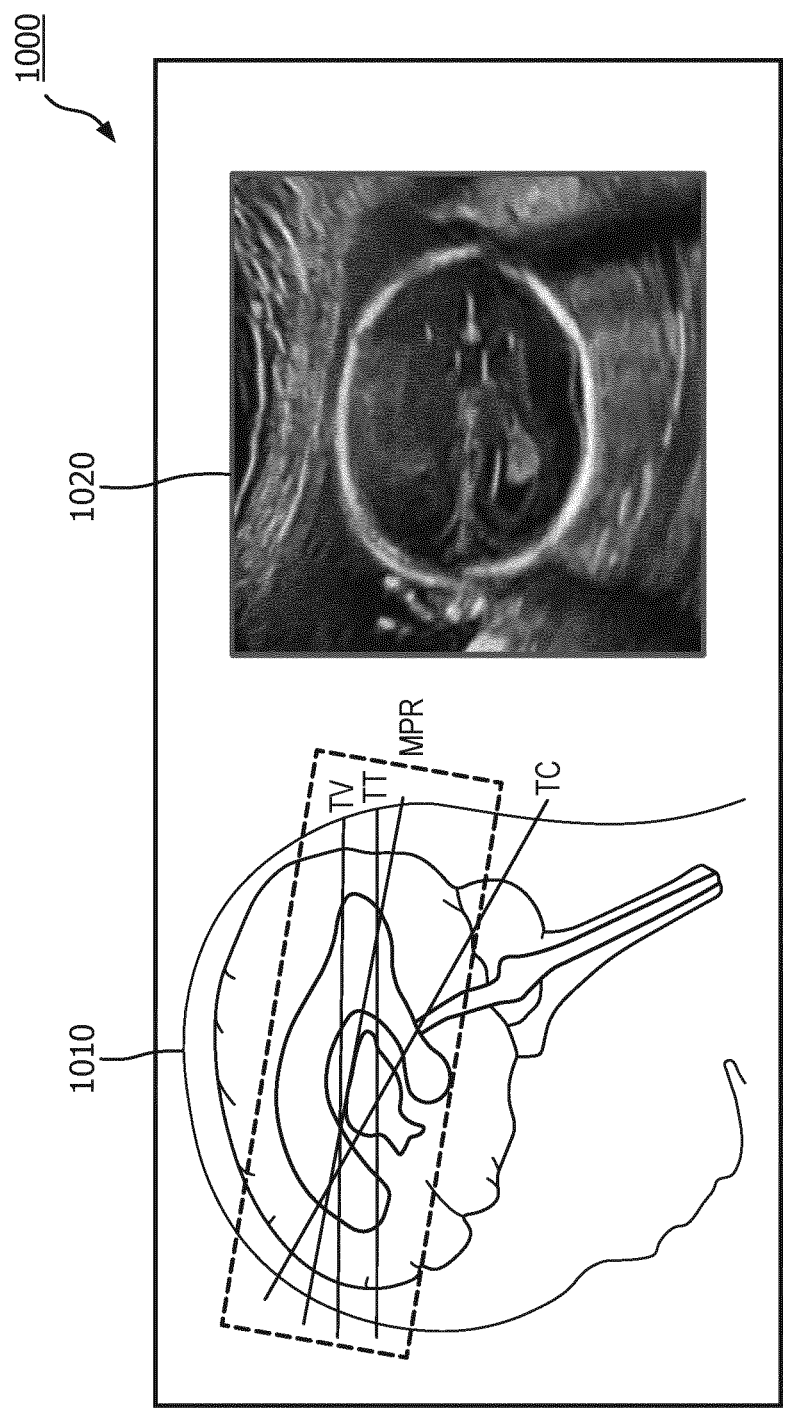
FIG. 9 is a screen of a graphical user interface that includes a reconstructed image frame corresponding to a target view, according to aspects of the present disclosure.

FIG. 9 is a graphical user interface (GUI) 1000 of an ultrasound imaging system, where the GUI includes an anatomical diagram 1010 of a body portion, and an MPR image 1020 of an image plane within the body portion. The anatomical diagram 1010 comprises a graphical representation of an anatomy of the patient (e.g., head of the fetus), and is annotated with indicators showing how various target image planes intersect the anatomy. In the illustrated embodiment, the body portion comprises a human head. For example, the diagram 1010 may be associated with a head of a fetus for use during a fetal ultrasound procedure. A plurality of line indicators is shown overlaid on the diagram of anatomy 1010. The line indicators are representative of various image planes or views of interest. In that regard, the views associated with the indicators include a trans-ventricular (TV) image plane, a trans-cerebellar (TC) image plane, and a trans-thalamic (TT) image plane. Another indicator is provided showing a reconstructed frame (MPR). In some embodiments, the MPR indicator may be a dynamic indicator that is responsive to input from a user provided using a user interface device. In the illustrated embodiment, the MPR indicator on the diagram 1010 corresponds to the MPR image 1020 shown beside the diagram 1010. For example, in some embodiments, the GUI 1000 may display a target image corresponding to one of the views shown in the diagram 1010. A user may interact with the GUI using a user interface device, such as a mouse, keyboard, track ball, voice input, touch screen input, or any other suitable input. The input from the user indicates a direction of motion along a simulated motion path. For example, the user input may be received in the form of a scrolling of the mouse, an arrow button on a keyboard, and/or scrolling of a track ball. The MPR indicator and the displayed MPR image 1020 can be updated in response to the received input to show adjacent MPR images reconstructed along the simulated motion path. A user may scan/scroll forward and backward along the path, and the MPR indicator may be updated in real time to show the location and orientation of the image plane associated with the MPR image 1020. The MPR image 1020 is also updated based on the user input to show the image corresponding to the MPR image plane illustrated with respect to the diagram 1010. Thus, the sonographer can control the display of the MPR images as if the user was manually scanning the ultrasound probe up and down a trajectory, but after the ultrasound image data has already been obtained. For example, the GUI 1000 may be provided after the sonographer has obtained the three-dimensional ultrasound data, and replaced the ultrasound probe Various modifications to the devices, systems, and/or methods described above could be made without departing from the scope of the present disclosure. For example, in some embodiments, the processor circuit is configured to display a looped playback of the target image and adjacent images to provide the appearance of periodically scanning forward and/or backward along the simulated motion path. In some embodiments, the processor circuit is configured to scan through a plurality of adjacent images in response to a single user input (e.g., key press, button press, etc.) In some embodiments, the processor circuit is configured to receive a user input to correct or adjust the reconstructed target image. For example, in some embodiments, the processor circuit may be configured to receive, from the sonographer via a user input device, a selection corresponding to an adjacent image. The processor circuit may then tag, save, or otherwise identify the selected adjacent image as the target image. In some embodiments, the target image comprises an interpolated image generated as described above. In some embodiments, the adjacent images are displayed successively, and one-by-one. In other embodiments, the adjacent images are displayed alongside the target image. In some embodiments, multiple adjacent and/or interpolated images are displayed simultaneously. In some embodiments, multiple different simulated motion paths are determined. For example, motion paths corresponding to different directions of uncertainty may be provided. In some embodiments, intersecting simulated motion paths are determined, as well as additional adjacent images associated with the intersecting simulated motion paths. Thus, in some embodiments, different inputs (e.g., up/down, left/right key presses) received through a user interface correspond to adjacent images along different simulated motions paths.

Embodiments of the present disclosure provide a number of benefits for automated image reconstruction procedures. For example, generating and displaying the dynamic adjacent image stream provides a familiar imaging experience, a simple and intuitive way to correct the target image, and a simple workflow transition from two-dimensional to three-dimensional ultrasound image acquisition. Further, embodiments of the present disclosure provide a user-friendly way to navigate between multiple planes of interest in one anatomy (e.g. TT, TV and TC planes for fetal ultrasound), and efficient ways to provide important anatomical context information and renderings directly related to the clinical guidelines for standard plane selection by use of anatomical objects to be or not to be included. Further, embodiments of the present disclosure allow for enhanced clinical confidence in an automatically reconstructed image.

It will be understood that one or more of the steps of the methods 300, 800, and 900 described above, may be performed by one or more components of an ultrasound imaging system, such as a processor or processor circuit, a multiplexer, a beamformer, a signal processing unit, an image processing unit, or any other suitable component of the system. For example, one or more steps described above may be carried out by the processor circuit 150 described with respect to FIG. 2. The processing components of the system can be integrated within the ultrasound imaging device, contained within an external console, or may be a separate component.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging apparatus, comprising:
   a processor circuit configured to:
   receive, from an ultrasound probe communicatively coupled to the processor circuit, three-dimensional (3D) ultrasound data of an anatomy;
   generate, from the 3D ultrasound data, a first two-dimensional (2D) image corresponding to a first image plane of the anatomy;
   determine a path intersecting the first 2D image;

generate, from the 3D ultrasound data, a second 2D image to have a first spatial relationship with the first 2D image that is defined by the path, wherein the second 2D image corresponds to a second image plane of the anatomy that is adjacent to the first image plane along the path, wherein the path intersects the second 2D image;

output, to a display in communication with the processor circuit, the first 2D image;

receive a user input representative of a direction of motion along the path; and output, to the display, the second 2D image in response to the user input, wherein the first 2D image is generated using multiplanar reconstruction (MPR), wherein the processor circuit is configured to:
  determine a direction of uncertainty associated with whether or not the first 2D image is representative of a target image plane; and
  determine the path based on the determined direction of uncertain.

2. The ultrasound imaging apparatus of claim 1, further comprising the ultrasound probe.

3. The ultrasound imaging apparatus of claim 1,
wherein the first 2D image and the second 2D image are generated using multiplanar reconstruction (MPR),
wherein the processor circuit is configured to:
  generate a third 2D image between the first 2D image and the second 2D image using interpolation; and
  output the third 2D image to the display.

4. The ultrasound imaging apparatus of claim 1, wherein the processor circuit is configured to apply a covariance matrix to the three-dimensional ultrasound data to determine the direction of uncertainty.

5. The ultrasound imaging apparatus of claim 1, wherein the second 2D image is parallel to the first 2D image.

6. The ultrasound imaging apparatus of claim 1,
wherein the processor circuit is configured to generate the first 2D image to exclude an anatomical feature, and
wherein the processor circuit is configured to generate the second 2D image to include the anatomical feature.

7. The ultrasound imaging apparatus of claim 1, wherein the processor circuit is further configured to output, to the display, a graphical representation of the second image plane associated with the second 2D image, wherein the graphical representation includes:
  a diagramatic view of a portion associated with the first 2D image; and
  an indicator of the second plane overlaid on the diagramatic view of the body portion.

8. The ultrasound imaging apparatus of claim 1,
wherein the ultrasound probe is configured to obtain the 3D ultrasound data while in a fixed position and orientation,
wherein the path is representative of a simulated physical adjustment or movement of the ultrasound probe.

9. The ultrasound imaging apparatus of claim 8, wherein the path comprises:
  a first segment representative of a first type of the simulated physical adjustment or movement; and
  a second segment representative of a second type of the simulated physical adjustment or movement.

10. The ultrasound imaging apparatus of claim 1,
wherein the 3D ultrasound data is obtained during an ultrasound procedure comprising a first image plane of interest and a second image plane of interest,
wherein the first image plane comprises the first image plane of interest,
wherein the processor circuit is configured to generate a further 2D image, and
wherein the path is generated based on the first image plane of interest and the second image plane of interest such that the further 2D image comprises the second image plane of interest.

11. The ultrasound imaging apparatus of claim 10, wherein the processor circuit is configured to output the further 2D image in response to receiving the user input.

12. The ultrasound imaging apparatus of claim 1,
wherein the processor circuit is configured to generate, from the 3D ultrasound data, a plurality of adjacent 2D images,
wherein each adjacent 2D image in the plurality of adjacent 2D images is generated to have a second spatial relationship with the first 2D image that is defined by the path, and
wherein each of the plurality of adjacent 2D images is associated with an adjacent image plane in a plurality of adjacent image planes.

13. The ultrasound imaging apparatus of claim 1,
wherein the processor circuit is configured to generate, from the 3D ultrasound data, a third 2D image to have a second spatial relationship with the first 2D image that is defined by the path, and
wherein the third 2D image corresponds to a third image plane of the anatomy, and
wherein the path intersects the third 2D image on a different side of the first 2D image than the path intersects the second 2D image.

14. The ultrasound imaging apparatus of claim 13, wherein the processor is configured to:
  output, to the display in communication with the processor circuit, the second 2D image when the user input indicates a direction from the first 2D image to the second 2D image, and
  output, to the display in communication with the processor circuit, the third 2D image when the user input indicates a direction from the first 2D image to the third 2D image.

15. An ultrasound imaging apparatus, comprising:
a processor circuit configured to:
  receive, from an ultrasound probe communicatively coupled to the processor circuit, three-dimensional (3D) ultrasound data of an anatomy;
  generate, from the 3D ultrasound data, a first two-dimensional (2D) image corresponding to a first image plane of the anatomy;
  determine a path intersecting the first 2D image;
  generate, from the 3D ultrasound data, a second 2D image to have a first spatial relationship with the first 2D image that is defined by the path, wherein the second 2D image corresponds to a second image plane of the anatomy that is adjacent to the first image plane along the path, wherein the path intersects the second 2D image;
  output, to a display in communication with the processor circuit, the first 2D image;
  receive a user input representative of a direction of motion along the path; and output, to the display, the second 2D image in response to the user input,
wherein the path comprises a first point, a second point, a first axis, and a second axis, wherein the first axis is tangent to the path at the first point and the second axis is tangent to the path at the second point, and wherein the first image plane includes the first point and the first axis is orthogonal to the first image plane at the first point.

16. The ultrasound imaging apparatus of claim 15, wherein the processor circuit is configured to determine the path using spline interpolation between the first point and the second point.

* * * * *